(12) United States Patent
Kang et al.

(10) Patent No.: US 12,029,805 B2
(45) Date of Patent: Jul. 9, 2024

(54) PROPERTIES FOR ACHIEVING LONG-LASTING COSMETIC PERFORMANCE

(71) Applicant: Living Proof, Inc., Boston, MA (US)

(72) Inventors: Soo-Young Kang, Bedford, MA (US); Zhaoxia Ji, Natick, MA (US); Ling-Fang Tseng, Boston, MA (US); Dinara A. Villanueva, Boston, MA (US); Sara A. Johnson, Boston, MA (US)

(73) Assignee: Living Proof, Inc., Boston, MA (US)

( * ) Notice: Subject to any disclaimer, the term of this patent is extended or adjusted under 35 U.S.C. 154(b) by 0 days.

(21) Appl. No.: 16/195,584

(22) Filed: Nov. 19, 2018

(65) Prior Publication Data

US 2019/0151221 A1 May 23, 2019

Related U.S. Application Data

(60) Provisional application No. 62/588,491, filed on Nov. 20, 2017.

(51) Int. Cl.
*A61K 8/73* (2006.01)
*A61K 8/81* (2006.01)
*A61Q 5/06* (2006.01)

(52) U.S. Cl.
CPC ............ *A61K 8/732* (2013.01); *A61K 8/8141* (2013.01); *A61K 8/8147* (2013.01); *A61K 8/8152* (2013.01); *A61K 8/8158* (2013.01); *A61K 8/817* (2013.01); *A61Q 5/06* (2013.01)

(58) Field of Classification Search
None
See application file for complete search history.

(56) References Cited

U.S. PATENT DOCUMENTS

| | | |
|---|---|---|
| 3,104,424 A | 9/1963 | Immel |
| 3,262,686 A | 7/1966 | Kraus et al. |
| 3,803,063 A | 4/1974 | Krentz, Jr. |
| 3,973,901 A | 8/1976 | Micchelli et al. |
| 4,071,614 A | 1/1978 | Grimm, III |
| 4,455,146 A | 6/1984 | Noda et al. |
| 4,950,542 A | 8/1990 | Barker |
| 5,110,852 A | 5/1992 | Gogolewski et al. |
| 5,281,654 A | 1/1994 | Eisenhart et al. |
| 5,290,543 A | 3/1994 | Ounanian et al. |
| 5,335,373 A | 8/1994 | Dresdner, Jr. et al. |
| 5,354,807 A | 10/1994 | Dochniak |
| 5,357,636 A | 10/1994 | Dresdner, Jr. et al. |
| 5,362,486 A | 11/1994 | Nandagiri et al. |
| 5,534,265 A | 7/1996 | Fowler et al. |
| 5,534,348 A | 7/1996 | Miller et al. |
| 5,540,853 A | 7/1996 | Trinh et al. |
| 5,626,840 A | 5/1997 | Thomaides et al. |
| 5,637,291 A | 6/1997 | Bara et al. |
| 5,643,581 A | 7/1997 | Mougin et al. |
| 5,720,961 A | 2/1998 | Fowler et al. |
| 5,733,572 A | 3/1998 | Unger et al. |
| 5,807,540 A | 9/1998 | Junino et al. |
| 5,833,967 A | 11/1998 | Ramin |
| 5,846,551 A | 12/1998 | DaCunha et al. |
| 5,849,310 A | 12/1998 | Trinh et al. |
| 5,891,463 A | 4/1999 | Bello et al. |
| 5,900,457 A | 5/1999 | Duan et al. |
| 5,912,299 A | 6/1999 | Tomko et al. |
| 5,914,117 A | 6/1999 | Lavaud |
| 5,932,194 A | 8/1999 | Plessix et al. |
| 5,932,200 A | 8/1999 | Reich et al. |
| 5,993,972 A | 11/1999 | Reich et al. |
| 6,007,793 A | 12/1999 | Bhatt et al. |
| 6,084,051 A | 7/2000 | Blum et al. |
| 6,086,903 A | 7/2000 | Trinh et al. |
| 6,106,813 A | 8/2000 | Mondet et al. |
| 6,126,930 A | 10/2000 | Dubois et al. |
| 6,130,309 A | 10/2000 | Reich et al. |
| 6,132,704 A | 10/2000 | Bhatt et al. |
| 6,153,179 A | 11/2000 | Blankenburg et al. |
| 6,156,325 A | 12/2000 | Farer et al. |
| 6,221,344 B1 | 4/2001 | Ramin et al. |
| 6,238,651 B1 | 5/2001 | Bara |
| 6,254,876 B1 | 7/2001 | de la Poterie et al. |
| 6,277,386 B1 | 8/2001 | Kim et al. |
| 6,277,401 B1 | 8/2001 | Bello et al. |
| 6,291,580 B1 | 9/2001 | Kukkala et al. |
| 6,298,558 B1 | 10/2001 | Tseng et al. |
| 6,319,959 B1 | 11/2001 | Mougin et al. |
| 6,326,013 B1 | 12/2001 | Lemann et al. |
| 6,346,234 B1 | 2/2002 | Rollat et al. |
| 6,361,782 B1 | 3/2002 | Chevalier et al. |

(Continued)

FOREIGN PATENT DOCUMENTS

| | | |
|---|---|---|
| BR | PI0405064 A | 8/2005 |
| BR | 102013022835 A2 | 8/2015 |

(Continued)

OTHER PUBLICATIONS

Copending U.S. Appl. No. 16/348,644, filed May 9, 2019.
Lochhead et al., Polymers in Cosmetics: Recent Advances. From film-formers to rheology modifiers, polymers serve various functions. Retrieved online at: https://www.happi.com/contents/view_features/2005-11-15/polymers-in-cosmetics-recent-advances. 12 pages, Nov. 15, 2005.
Srivastava et al., Indian Application No. 148/DEL/2010. Bioreactor and Uses Thereof. Filed Jul. 29, 2011. 20 pages.
Teixeira et al., A case study of product engineering: Performance of microencapsulated perfumes on textile applications. AIChE Journal. Jun. 2011;58(6):1939-1950.
Invitation to Pay Additional Fees for Application No. PCT/US2018/050546, dated Jan. 7, 2019, 15 pages.

(Continued)

*Primary Examiner* — Brian Gulledge
(74) *Attorney, Agent, or Firm* — McCarter & English, LLP; Michael J. DeGrazia (57) ABSTRACT

Provided herein are long lasting hair styling compositions and markers for selecting the same.

14 Claims, 3 Drawing Sheets

(56) References Cited

U.S. PATENT DOCUMENTS

| | | |
|---|---|---|
| 6,365,697 B1 | 4/2002 | Kim et al. |
| 6,372,876 B1 | 4/2002 | Kim et al. |
| 6,403,070 B1 | 6/2002 | Pataut et al. |
| 6,403,107 B1 | 6/2002 | Lemann |
| 6,403,542 B1 | 6/2002 | Maurin et al. |
| 6,409,998 B1 | 6/2002 | Candau et al. |
| 6,433,073 B1 | 8/2002 | Kantner et al. |
| 6,465,534 B2 | 10/2002 | Fukuzawa et al. |
| 6,469,227 B1 | 10/2002 | Cooke et al. |
| 6,485,950 B1 | 11/2002 | Kumar et al. |
| 6,517,821 B1 | 2/2003 | Rollat et al. |
| 6,520,186 B2 | 2/2003 | Rollat et al. |
| 6,524,564 B1 | 2/2003 | Kim et al. |
| 6,524,597 B2 | 2/2003 | Kashimoto |
| 6,531,118 B1 | 3/2003 | Gonzalez et al. |
| 6,555,096 B2 | 4/2003 | Carrion et al. |
| 6,576,024 B1 | 6/2003 | Lang et al. |
| 6,576,702 B2 | 6/2003 | Anderle et al. |
| 6,579,517 B1 | 6/2003 | Kim et al. |
| 6,592,881 B1 | 7/2003 | Fukuda et al. |
| 6,613,314 B1 | 9/2003 | Rollat et al. |
| 6,635,262 B2 | 10/2003 | Jourdan et al. |
| 6,641,804 B1 | 11/2003 | Ohta et al. |
| 6,682,748 B1 | 1/2004 | De La Poterie et al. |
| 6,689,345 B2 | 2/2004 | Jager Lezer |
| 6,692,729 B1 | 2/2004 | Asaoka et al. |
| 6,719,959 B1 | 4/2004 | Gonzalez et al. |
| 6,730,289 B2 | 5/2004 | Khoshdel |
| 6,750,291 B2 | 6/2004 | Kim et al. |
| 6,800,276 B2 | 10/2004 | Kim et al. |
| 6,830,758 B2 | 12/2004 | Nichols et al. |
| 6,884,853 B1 | 4/2005 | Asaoka et al. |
| 6,897,281 B2 | 5/2005 | Lubnin et al. |
| 6,927,254 B2 | 8/2005 | Melchiors et al. |
| 7,019,061 B2 | 3/2006 | Meffert et al. |
| 7,098,178 B2 | 8/2006 | Gerke et al. |
| 7,101,954 B2 | 9/2006 | Zofchak et al. |
| 7,160,553 B2 | 1/2007 | Gibbins et al. |
| 7,326,256 B2 | 2/2008 | Cottard et al. |
| 7,348,299 B2 | 3/2008 | Keenan et al. |
| 7,445,770 B2 | 11/2008 | Berezkin et al. |
| 7,452,525 B1 | 11/2008 | Berezkin et al. |
| 7,481,996 B2 | 1/2009 | Ishii et al. |
| 7,659,233 B2 | 2/2010 | Hurley et al. |
| 7,700,082 B2 | 4/2010 | Mallo et al. |
| 7,740,832 B1 | 6/2010 | Rollat-Corvol et al. |
| 7,744,911 B2 | 6/2010 | Pechko et al. |
| RE41,615 E | 8/2010 | Kim et al. |
| 7,829,099 B2 | 11/2010 | Woeller et al. |
| 7,907,346 B2 | 3/2011 | Swarup et al. |
| 7,914,775 B2 | 3/2011 | Cottard et al. |
| 7,959,903 B2 | 6/2011 | Candau et al. |
| 7,972,589 B2 | 7/2011 | Leighton et al. |
| 7,998,465 B2 | 8/2011 | De La Poterie et al. |
| 8,067,355 B2 | 11/2011 | Smets et al. |
| 8,258,093 B2 | 9/2012 | Van Dyke |
| 8,343,523 B2 | 1/2013 | Toreki et al. |
| 8,449,871 B2 | 5/2013 | Mougin et al. |
| 8,497,338 B2 | 7/2013 | Bai et al. |
| 8,623,388 B2 | 1/2014 | Rajaiah et al. |
| 8,629,213 B2 | 1/2014 | Hidalgo et al. |
| 8,679,050 B2 | 3/2014 | Nakamura |
| 8,679,465 B2 | 3/2014 | Malnou et al. |
| 8,685,377 B2 | 4/2014 | Kaftan et al. |
| 8,734,772 B1 | 5/2014 | Zhou et al. |
| 8,741,333 B2 | 6/2014 | Zhang et al. |
| 8,784,854 B2 | 7/2014 | Choi et al. |
| 8,871,817 B2 | 10/2014 | Turk et al. |
| 8,882,902 B2 | 11/2014 | Suzuki et al. |
| 8,895,040 B2 | 11/2014 | Vondruska et al. |
| 8,956,160 B2 | 2/2015 | Willison et al. |
| 8,956,162 B2 | 2/2015 | De Vreese et al. |
| 9,016,221 B2 | 4/2015 | Brennan et al. |
| RE45,538 E | 6/2015 | Smets et al. |
| 9,079,152 B2 | 7/2015 | Markus et al. |
| 9,101,143 B2 | 8/2015 | Markus et al. |
| 9,102,783 B2 | 8/2015 | Yagi et al. |
| 9,175,125 B2 | 11/2015 | Turk et al. |
| 9,295,632 B1 | 3/2016 | Benn et al. |
| 9,340,650 B2 | 5/2016 | Wagner et al. |
| 9,393,218 B2 | 7/2016 | Zurdo Schroeder et al. |
| 9,458,354 B2 | 10/2016 | Felice et al. |
| 2001/0031280 A1 | 10/2001 | Ferrari et al. |
| 2002/0028875 A1 | 3/2002 | Anderle et al. |
| 2002/0034480 A1 | 3/2002 | Grimm et al. |
| 2002/0034486 A1 | 3/2002 | Midha et al. |
| 2002/0102222 A1 | 8/2002 | Carrion et al. |
| 2002/0107314 A1 | 8/2002 | Pinzon et al. |
| 2002/0114773 A1 | 8/2002 | Kanji et al. |
| 2002/0155962 A1 | 10/2002 | Cincotta et al. |
| 2002/0164297 A1 | 11/2002 | Ferrari et al. |
| 2002/0192273 A1 | 12/2002 | Buseman et al. |
| 2003/0026815 A1 | 2/2003 | Scott et al. |
| 2003/0064086 A1 | 4/2003 | Carrion et al. |
| 2003/0082126 A9 | 5/2003 | Pinzon et al. |
| 2003/0086886 A1 | 5/2003 | Midha |
| 2003/0086896 A1 | 5/2003 | Midha et al. |
| 2003/0099694 A1 | 5/2003 | Cevc et al. |
| 2003/0125427 A9 | 7/2003 | Pinzon et al. |
| 2003/0185780 A1 | 10/2003 | Ferrari et al. |
| 2003/0190345 A1 | 10/2003 | Cordes et al. |
| 2003/0191154 A1 | 10/2003 | Kalafsky et al. |
| 2003/0198659 A1 | 10/2003 | Hoffmann et al. |
| 2003/0203991 A1 | 10/2003 | Schottman et al. |
| 2004/0001798 A1 | 1/2004 | Perron et al. |
| 2004/0057914 A1 | 3/2004 | Bonda et al. |
| 2004/0071757 A1 | 4/2004 | Rolf |
| 2004/0086482 A1 | 5/2004 | Zofchak et al. |
| 2004/0120915 A1 | 6/2004 | Yang et al. |
| 2004/0131573 A1 | 7/2004 | Tang |
| 2004/0137028 A1 | 7/2004 | de la Poterie |
| 2004/0156804 A1 | 8/2004 | Poterie et al. |
| 2004/0166076 A1 | 8/2004 | Ferrari et al. |
| 2004/0166133 A1 | 8/2004 | Cavazzuti et al. |
| 2004/0176487 A1 | 9/2004 | Svedberg et al. |
| 2004/0186259 A1 | 9/2004 | Brehm et al. |
| 2004/0197286 A1 | 10/2004 | Robert et al. |
| 2004/0223987 A1 | 11/2004 | Ferrari |
| 2004/0228886 A1 | 11/2004 | Ding et al. |
| 2004/0247549 A1 | 12/2004 | Lu et al. |
| 2005/0008667 A1 | 1/2005 | Liechty et al. |
| 2005/0014674 A1 | 1/2005 | Liechty et al. |
| 2005/0043209 A1 | 2/2005 | Schmiedel et al. |
| 2005/0089540 A1 | 4/2005 | Uchiyama et al. |
| 2005/0118126 A1 | 6/2005 | Rollat et al. |
| 2005/0148753 A1 | 7/2005 | Nguyen-Kim et al. |
| 2005/0163741 A1 | 7/2005 | Zech |
| 2005/0169873 A1 | 8/2005 | Rollat et al. |
| 2005/0169874 A1 | 8/2005 | Zofchak et al. |
| 2005/0209428 A1 | 9/2005 | Tamareselvy |
| 2005/0220740 A1 | 10/2005 | Dumousseaux |
| 2005/0220741 A1 | 10/2005 | Dumousseaux |
| 2005/0249691 A1 | 11/2005 | Monks et al. |
| 2005/0257330 A1 | 11/2005 | Noecker et al. |
| 2005/0276831 A1 | 12/2005 | Dihora et al. |
| 2005/0287100 A1 | 12/2005 | Lebre |
| 2005/0287103 A1 | 12/2005 | Filippi et al. |
| 2005/0287182 A1 | 12/2005 | Monks et al. |
| 2005/0287183 A1 | 12/2005 | Lebre |
| 2006/0045890 A1 | 3/2006 | Gonzalez et al. |
| 2006/0045893 A1 | 3/2006 | Yu et al. |
| 2006/0051311 A1 | 3/2006 | Walter et al. |
| 2006/0073106 A1 | 4/2006 | Berg-Schultz et al. |
| 2006/0078519 A1 | 4/2006 | Lion et al. |
| 2006/0083762 A1 | 4/2006 | Brun et al. |
| 2006/0099550 A1 | 5/2006 | Faasse et al. |
| 2006/0120983 A1 | 6/2006 | Blin et al. |
| 2006/0134049 A1 | 6/2006 | Keenan et al. |
| 2006/0171984 A1 | 8/2006 | Cromack et al. |
| 2006/0193789 A1 | 8/2006 | Tamarkin et al. |
| 2006/0216250 A1 | 9/2006 | Schultz et al. |
| 2006/0233728 A1 | 10/2006 | Sagawa et al. |
| 2006/0281650 A1 | 12/2006 | Keenan et al. |
| 2006/0287219 A1 | 12/2006 | Dykstra et al. |

(56) References Cited

U.S. PATENT DOCUMENTS

| | | |
|---|---|---|
| 2007/0032605 A1 | 2/2007 | Harashina |
| 2007/0105977 A1 | 5/2007 | Gabriel et al. |
| 2007/0167565 A1 | 7/2007 | Rische et al. |
| 2007/0183992 A1 | 8/2007 | Dumousseaux et al. |
| 2007/0183997 A9 | 8/2007 | Lebre et al. |
| 2007/0189980 A1 | 8/2007 | Zhang et al. |
| 2007/0197704 A1 | 8/2007 | Walter et al. |
| 2007/0207222 A1 | 9/2007 | Yu et al. |
| 2007/0251026 A1 | 11/2007 | Lalleman et al. |
| 2008/0044373 A1 | 2/2008 | Ilekti et al. |
| 2008/0044445 A1 | 2/2008 | Rubin |
| 2008/0045985 A1 | 2/2008 | Gurtner et al. |
| 2008/0138368 A1 | 6/2008 | Lezer |
| 2008/0175875 A1 | 7/2008 | Sunkara |
| 2008/0254074 A1 | 10/2008 | Dussaud et al. |
| 2009/0041683 A1 | 2/2009 | Molenda et al. |
| 2009/0049623 A1 | 2/2009 | Brown et al. |
| 2009/0056734 A1 | 3/2009 | Bacon |
| 2009/0061004 A1 | 3/2009 | Birkel et al. |
| 2009/0105195 A1 | 4/2009 | O'Brien |
| 2009/0112141 A1 | 4/2009 | Derr |
| 2009/0175928 A1 | 7/2009 | Maier et al. |
| 2009/0196842 A1 | 8/2009 | Zech et al. |
| 2009/0257960 A1 | 10/2009 | Kim et al. |
| 2009/0263338 A1 | 10/2009 | Rolland et al. |
| 2009/0285866 A1 | 11/2009 | Afriat et al. |
| 2010/0003198 A1 | 1/2010 | Stolmeier et al. |
| 2010/0233146 A1 | 9/2010 | McDaniel |
| 2010/0260687 A1 | 10/2010 | Yu et al. |
| 2010/0261629 A1 | 10/2010 | Smets et al. |
| 2010/0297036 A1 | 11/2010 | Feuillette |
| 2010/0325812 A1 | 12/2010 | Panandiker et al. |
| 2010/0325813 A1 | 12/2010 | Dykstra et al. |
| 2011/0010817 A1 | 1/2011 | Theberge et al. |
| 2011/0027211 A1 | 2/2011 | Viala et al. |
| 2011/0046286 A1 | 2/2011 | Lubnin et al. |
| 2011/0117042 A1 | 5/2011 | Viala et al. |
| 2011/0200927 A1 | 8/2011 | Jung et al. |
| 2011/0229430 A1 | 9/2011 | Hawkins et al. |
| 2011/0230474 A1 | 9/2011 | Grigorian et al. |
| 2011/0256311 A1 | 10/2011 | Mattos, Jr. |
| 2011/0272320 A1 | 11/2011 | Alwattari et al. |
| 2011/0274633 A1 | 11/2011 | Vu et al. |
| 2012/0207696 A1 | 8/2012 | van Geel et al. |
| 2012/0255574 A1 | 10/2012 | Flohr et al. |
| 2013/0084256 A1 | 4/2013 | Li et al. |
| 2013/0161349 A1 | 6/2013 | Pfeiffenberger |
| 2013/0196849 A1 | 8/2013 | Combs et al. |
| 2013/0239344 A1 | 9/2013 | Stolarz, Jr. et al. |
| 2013/0239874 A1 | 9/2013 | Smith et al. |
| 2013/0261255 A1 | 10/2013 | Deyrail et al. |
| 2013/0344019 A1 | 12/2013 | Weber et al. |
| 2014/0010776 A1 | 1/2014 | Viala et al. |
| 2014/0044657 A1 | 2/2014 | Kelly et al. |
| 2014/0066496 A1 | 3/2014 | Gunari et al. |
| 2014/0086864 A1 | 3/2014 | Ishimori et al. |
| 2014/0105846 A1 | 4/2014 | Viala et al. |
| 2014/0142191 A1 | 5/2014 | De La Zerda et al. |
| 2014/0147396 A1 | 5/2014 | Sertchook et al. |
| 2014/0170327 A1 | 6/2014 | Dombrowski et al. |
| 2014/0219927 A1 | 8/2014 | Belluscio et al. |
| 2014/0248270 A1 | 9/2014 | Yu et al. |
| 2014/0248340 A1 | 9/2014 | Schwarzentruber et al. |
| 2014/0350269 A1 | 11/2014 | Eiji Borges Sato |
| 2015/0004117 A1* | 1/2015 | Tan ............... A61K 8/87 424/70.16 |
| 2015/0004200 A1 | 1/2015 | Brown et al. |
| 2015/0007849 A1 | 1/2015 | Cajan et al. |
| 2015/0071978 A1 | 3/2015 | Chang |
| 2015/0118331 A1 | 4/2015 | Boam et al. |
| 2015/0119497 A1 | 4/2015 | Matsui et al. |
| 2015/0190450 A1 | 7/2015 | Chang |
| 2015/0238406 A1 | 8/2015 | Pohlmann et al. |
| 2015/0283041 A1* | 10/2015 | Benn ............... A61K 8/19 424/70.5 |
| 2015/0342845 A1 | 12/2015 | Hwang et al. |
| 2015/0344622 A1 | 12/2015 | Mukerjee et al. |
| 2016/0001099 A1 | 1/2016 | Castro et al. |
| 2016/0058678 A1 | 3/2016 | Smets et al. |
| 2016/0074311 A1 | 3/2016 | Massey-Brooker et al. |
| 2016/0143836 A1 | 5/2016 | Hayes et al. |
| 2016/0175233 A1 | 6/2016 | Benn |
| 2016/0175238 A1 | 6/2016 | Shin et al. |
| 2016/0184195 A1 | 6/2016 | Tan et al. |
| 2016/0220475 A1 | 8/2016 | Scherner et al. |
| 2017/0216188 A1 | 8/2017 | Bermudez Agudelo et al. |
| 2017/0258700 A1 | 9/2017 | Kang et al. |
| 2018/0000699 A1 | 1/2018 | Trahan |
| 2019/0076347 A1 | 3/2019 | Kang et al. |
| 2019/0076348 A1 | 3/2019 | Kang et al. |
| 2019/0359786 A1 | 11/2019 | Trahan et al. |
| 2021/0212920 A1 | 7/2021 | Kang et al. |
| 2022/0105021 A1 | 4/2022 | Kang et al. |

FOREIGN PATENT DOCUMENTS

| | | |
|---|---|---|
| CN | 1236783 A | 12/1999 |
| CN | 1370063 A | 9/2002 |
| CN | 1370185 A | 9/2002 |
| CN | 1413102 A | 4/2003 |
| CN | 1476320 A | 2/2004 |
| CN | 1487962 A | 4/2004 |
| CN | 1607934 A | 4/2005 |
| CN | 1650840 A | 8/2005 |
| CN | 1708524 A | 12/2005 |
| CN | 1775826 A | 5/2006 |
| CN | 101124256 A | 2/2008 |
| CN | 101130082 A | 2/2008 |
| CN | 101361701 A | 2/2009 |
| CN | 101484130 A | 7/2009 |
| CN | 101980691 A | 2/2011 |
| CN | 102015803 A | 4/2011 |
| CN | 102575051 A | 7/2012 |
| CN | 102895164 A | 1/2013 |
| CN | 103314025 A | 9/2013 |
| CN | 103705401 A | 4/2014 |
| CN | 104188877 A | 12/2014 |
| CN | 105213260 A | 1/2016 |
| CN | 105561841 A | 5/2016 |
| CN | 105764484 A | 7/2016 |
| CN | 109071750 A | 12/2018 |
| DE | 102015204154 A1 | 9/2016 |
| EP | 727981 A1 | 8/1996 |
| EP | 789550 A1 | 8/1997 |
| EP | 923927 A1 | 6/1999 |
| EP | 1058560 A1 | 12/2000 |
| EP | 1082953 A1 | 3/2001 |
| EP | 1090632 A1 | 4/2001 |
| EP | 1090633 A1 | 4/2001 |
| EP | 1092419 A1 | 4/2001 |
| EP | 1155676 A2 | 11/2001 |
| EP | 1161937 A2 | 12/2001 |
| EP | 1216690 A2 | 6/2002 |
| EP | 1218430 A1 | 7/2002 |
| EP | 1289363 A1 | 3/2003 |
| EP | 1417886 A1 | 5/2004 |
| EP | 1419759 A2 | 5/2004 |
| EP | 1440680 A1 | 7/2004 |
| EP | 1481661 A2 | 12/2004 |
| EP | 1491179 A2 | 12/2004 |
| EP | 1579841 A1 | 9/2005 |
| EP | 1579849 A1 | 9/2005 |
| EP | 1598046 A1 | 11/2005 |
| EP | 1604634 A1 | 12/2005 |
| EP | 1707182 A1 | 10/2006 |
| EP | 1707183 A1 | 10/2006 |
| EP | 1773906 A1 | 4/2007 |
| EP | 1800671 A1 | 6/2007 |
| EP | 1903065 A2 | 3/2008 |
| EP | 2209472 A1 | 7/2010 |
| EP | 2271304 A1 | 1/2011 |
| EP | 2391424 A2 | 12/2011 |
| EP | 2591772 A1 | 5/2013 |
| EP | 2611466 A2 | 7/2013 |

(56) References Cited

FOREIGN PATENT DOCUMENTS

| | | |
|---|---|---|
| EP | 2726067 A1 | 5/2014 |
| EP | 2858630 A1 | 4/2015 |
| EP | 2859794 A1 | 4/2015 |
| EP | 2867298 A1 | 5/2015 |
| EP | 2925296 A1 | 10/2015 |
| EP | 2995217 A1 | 3/2016 |
| EP | 3020454 A1 | 5/2016 |
| FR | 2801209 A1 | 5/2001 |
| FR | 2815350 A1 | 4/2002 |
| FR | 2816834 A1 | 5/2002 |
| FR | 2835529 A1 | 8/2003 |
| FR | 2892931 A1 | 5/2007 |
| FR | 2902655 A1 | 12/2007 |
| FR | 2940093 A1 | 6/2010 |
| FR | 2957347 A1 | 9/2011 |
| FR | 2967062 A1 | 5/2012 |
| JP | H06362 A | 1/1994 |
| JP | H1080973 A | 3/1998 |
| JP | 2002-020451 A | 1/2002 |
| JP | 2003-081742 A | 3/2003 |
| JP | 2004-203917 A | 7/2004 |
| JP | 2004-256694 A | 9/2004 |
| JP | 2006-290845 A | 10/2006 |
| JP | 2009-292854 A | 12/2009 |
| JP | 2010-132568 A | 6/2010 |
| JP | 2010-163389 A | 7/2010 |
| JP | 2011-173851 A | 9/2011 |
| JP | 2011-246352 A | 12/2011 |
| JP | 2012-057110 A | 3/2012 |
| JP | 2013-502494 A | 1/2013 |
| JP | 2016-094362 A | 5/2016 |
| KR | 20080064230 A | 7/2008 |
| KR | 20090058294 A | 6/2009 |
| KR | 20090081582 A | 7/2009 |
| KR | 20110062277 A | 6/2011 |
| KR | 20140078356 A | 6/2014 |
| KR | 20140093349 A | 7/2014 |
| KR | 20140121154 A | 10/2014 |
| WO | 1989/007959 A1 | 9/1989 |
| WO | 1991/001970 A2 | 2/1991 |
| WO | 1994/13354 A1 | 6/1994 |
| WO | 1998/13025 A1 | 4/1998 |
| WO | 1998/26751 A1 | 6/1998 |
| WO | 1998/26756 A1 | 6/1998 |
| WO | 1999/12519 A1 | 3/1999 |
| WO | 1999/55288 A1 | 11/1999 |
| WO | 1999/55290 A1 | 11/1999 |
| WO | 1999/55291 A1 | 11/1999 |
| WO | 1999/55292 A1 | 11/1999 |
| WO | 1999/56708 A1 | 11/1999 |
| WO | 2000/14091 A1 | 3/2000 |
| WO | 2000/016752 A2 | 3/2000 |
| WO | 2000/018367 A1 | 4/2000 |
| WO | 2000/027350 A1 | 5/2000 |
| WO | 2000/40628 A1 | 7/2000 |
| WO | 2001/003652 A2 | 1/2001 |
| WO | 2001/024768 A2 | 4/2001 |
| WO | 2001/068037 A2 | 9/2001 |
| WO | 2001/078691 A1 | 10/2001 |
| WO | 2001/087065 A1 | 11/2001 |
| WO | 2001/094438 A1 | 12/2001 |
| WO | 2002/007699 A1 | 1/2002 |
| WO | 2002/039961 A1 | 5/2002 |
| WO | 2002/039964 A1 | 5/2002 |
| WO | 2002/043490 A1 | 6/2002 |
| WO | 2002/043491 A1 | 6/2002 |
| WO | 2002/045663 A1 | 6/2002 |
| WO | 2002/047620 A2 | 6/2002 |
| WO | 2002/047624 A1 | 6/2002 |
| WO | 2002/047626 A1 | 6/2002 |
| WO | 2002/047628 A1 | 6/2002 |
| WO | 2002/047657 A2 | 6/2002 |
| WO | 2002/047658 A2 | 6/2002 |
| WO | 2002/054997 A1 | 7/2002 |
| WO | 2002/055034 A2 | 7/2002 |
| WO | 2002/072045 A2 | 9/2002 |
| WO | 2003/028678 A1 | 4/2003 |
| WO | 2003/094870 A1 | 11/2003 |
| WO | 2004/110401 A2 | 12/2004 |
| WO | 2005/014777 A2 | 2/2005 |
| WO | 2005/017134 A2 | 2/2005 |
| WO | 2005/092963 A1 | 10/2005 |
| WO | 2006/015718 A1 | 2/2006 |
| WO | 2006/062740 A2 | 6/2006 |
| WO | 2006/127883 A2 | 11/2006 |
| WO | 2006/131403 A1 | 12/2006 |
| WO | 2007/057059 A1 | 5/2007 |
| WO | 2007/070643 A2 | 6/2007 |
| WO | 2007/071886 A2 | 6/2007 |
| WO | 2007/077029 A1 | 7/2007 |
| WO | 2007/145395 A1 | 12/2007 |
| WO | 2008/006677 A1 | 1/2008 |
| WO | 2008/006687 A1 | 1/2008 |
| WO | 2008/024408 A2 | 2/2008 |
| WO | 2008/125406 A2 | 10/2008 |
| WO | 2008/133982 A2 | 11/2008 |
| WO | 2008/148809 A1 | 12/2008 |
| WO | 2009/014347 A2 | 1/2009 |
| WO | 2009/053594 A2 | 4/2009 |
| WO | 2010/003138 A1 | 1/2010 |
| WO | 2010/006442 A1 | 1/2010 |
| WO | 2010/037402 A1 | 4/2010 |
| WO | 2010/076483 A1 | 7/2010 |
| WO | 2010/079468 A2 | 7/2010 |
| WO | 2010/086754 A2 | 8/2010 |
| WO | 2010/129299 A2 | 11/2010 |
| WO | 2011/016140 A1 | 2/2011 |
| WO | 2011/016531 A1 | 2/2011 |
| WO | 2011/022582 A1 | 2/2011 |
| WO | 2011/075556 A1 | 6/2011 |
| WO | 2011/089709 A1 | 7/2011 |
| WO | 2011/126978 A1 | 10/2011 |
| WO | 2011/140330 A2 | 11/2011 |
| WO | 2012/037445 A2 | 3/2012 |
| WO | 2012/063947 A1 | 5/2012 |
| WO | 2012/087510 A1 | 6/2012 |
| WO | 2012/105096 A1 | 8/2012 |
| WO | 2012/117013 A1 | 9/2012 |
| WO | 2012/121704 A1 | 9/2012 |
| WO | 2012/168102 A2 | 12/2012 |
| WO | 2013/064596 A1 | 5/2013 |
| WO | 2013/068478 A1 | 5/2013 |
| WO | 2013/071079 A1 | 5/2013 |
| WO | 2013/149323 A1 | 10/2013 |
| WO | 2013/165424 A1 | 11/2013 |
| WO | 2014/001574 A1 | 1/2014 |
| WO | 2014/001985 A1 | 1/2014 |
| WO | 2014/014139 A1 | 1/2014 |
| WO | 2014/105676 A1 | 7/2014 |
| WO | 2014/111579 A2 | 7/2014 |
| WO | 2014/176515 A2 | 10/2014 |
| WO | 2014/210117 A1 | 12/2014 |
| WO | 2015/020060 A1 | 2/2015 |
| WO | 2015/028417 A1 | 3/2015 |
| WO | 2015/028418 A1 | 3/2015 |
| WO | 2015/028421 A1 | 3/2015 |
| WO | 2015/028424 A1 | 3/2015 |
| WO | 2015/051139 A1 | 4/2015 |
| WO | 2015/188335 A1 | 12/2015 |
| WO | 2016/016315 A1 | 2/2016 |
| WO | 2016/058958 A1 | 4/2016 |
| WO | 2016/069396 A2 | 5/2016 |
| WO | 2016/074683 A1 | 5/2016 |
| WO | 2016/087948 A1 | 6/2016 |
| WO | 2016/096928 A1 | 6/2016 |
| WO | 2016/100885 A1 | 6/2016 |
| WO | 2016/115257 A2 | 7/2016 |
| WO | 2016/138249 A1 | 9/2016 |
| WO | 2017/112521 A1 | 6/2017 |
| WO | 2017/155906 A1 | 9/2017 |
| WO | 2019/210121 A1 | 10/2019 |

(56) References Cited

OTHER PUBLICATIONS

International Search Report and Written Opinion for Application No. PCT/US2018/050538, dated Jan. 7, 2019, 17 pages.
International Search Report and Written Opinion for Application No. PCT/US2017/021025, dated May 23, 2017.
Adina, Natpure Hollowbead. Adina Cosmetic Ingredients Ltd., retrieved online at: http://www.cosmeticingredients.co.uk/ingredient/natpure-hollowbead. 2 pages, (2015).
Akzonobel, Product Specification for Expancel Microspheres. www.expancel.com, 2 pages, (2011).
Araujo et al., Techniques for reducing residual monomer content in polymers: a review. Polymer Engineering and Science. 64 pages, Jul. 1, 2002.
U.S. Appl. No. 16/128,620, filed Sep. 12, 2018, 2019-0076347.
U.S. Appl. No. 16/128,622, filed Sep. 12, 2018, 2019-0076348.
U.S. Appl. No. 15/451,897, filed Mar. 7, 2017, 2017-0258700.
U.S. Appl. No. 16/348,644, filed May 9, 2019, 2019-0359786.
U.S. Appl. No. 16/128,620, filed Sep. 12, 2018, now U.S. Pat. No. 10,987,300.
U.S. Appl. No. 17/231,587, filed Apr. 15, 2021.
U.S. Appl. No. 16/128,622, filed Sep. 12, 2018, U.S. Pat. No. 10,842,729.
U.S. Appl. No. 17/071,198, filed Oct. 15, 2020.
U.S. Appl. No. 17/326,605, filed May 21, 2021.
U.S. Appl. No. 17/050,803, filed Oct. 26, 2020, 2021-0212920.
Xu et al., Synthesis and Characterization of Cationic Waterborne Polyurethane based Polycarbonate Polyol. China Leather. Nov. 2011;40(21):1-14.
Yao et al., Application of bionic technology in textiles. Textile Dyeing and Finishing Journal. Dec. 2013;35(12):29-33.
Zhang et al., Working Manual of Large Scale Poultry Farm Laboratory. Golden Shield Publishing House. p. 138, Oct. 2013.
Chinese Office Action for Application No. 201880058933.2, dated Aug. 4, 2021, 26 pages.
U.S. Appl. No. 15/451,897, filed Mar. 7, 2017, U.S. Pat. No. 11,622,929, Issued.
U.S. Appl. No. 18/114,425, filed Feb. 27, 2023, Abandoned.
U.S. Appl. No. 18/387,220, filed Nov. 6, 2023, Pending.
U.S. Appl. No. 16/348,644, filed May 9, 2019, Publication No. 2019-0359786, Abandoned.
U.S. Appl. No. 16/128,620, filed Sep. 12, 2018, U.S. Pat. No. 10,987,300, Issued.
U.S. Appl. No. 17/231,587, filed Apr. 15, 2021, Abandoned.
U.S. Appl. No. 17/530,662, filed Nov. 19, 2021, Abandoned.
U.S. Appl. No. 17/855,239, filed Jun. 30, 2022, Abandoned.
U.S. Appl. No. 18/168,215, filed Feb. 13, 2023, Abandoned.
U.S. Appl. No. 18/377,654, filed Oct. 6, 2023, Pending.
U.S. Appl. No. 16/128,622, filed filed Sep. 12, 2018, U.S. Pat. No. 10,842,729, Issued.
U.S. Appl. No. 17/071,198, filed Oct. 15, 2020, Abandoned.
U.S. Appl. No. 17/326,605, filed May 21, 2021, U.S. Pat. No. 11,707,426, Issued.
U.S. Appl. No. 18/206,908, filed Jun. 7, 2023, Pending.
U.S. Appl. No. 18/423,862, filed Jan. 26, 2024, Pending.
U.S. Appl. No. 17/050,803, filed Oct. 26, 2020, Publication No. 2021-0212920, Published.
Ma et al., Synthetic Leather Chemistry and Technology, 1st Edition. 4 pages, Nov. 30, 2015.
Rahman, Synthesis and properties of waterborne polyurethane adhesives: effect of chain extender of ethylene diamine, butfanediol, and fluoro-butanediol. Journal of Adhesion Science and Technology. 2013;27(23):2592-2602.
Chinese Office Action for Application No. 201980028764.2, dated Dec. 6, 2022, 17 pages.

\* cited by examiner

PROPERTIES FOR ACHIEVING LONG-LASTING COSMETIC PERFORMANCE

RELATED APPLICATIONS

This application claims the benefit of priority to U.S. Provisional Application No. 62/588,491, filed Nov. 20, 2017, the entire contents of which are incorporated herein by reference.

BACKGROUND

Hair styling or hair fixative compositions are widely used to retain a particular shape or style of the hair. Unfortunately, even after expensive and lengthy styling sessions, very few products exist which provide adequate protection against style loss, particularly in environmental conditions such as high humidity. As any consumer in the cosmetic industry with wavy or curly hair would know, dampness and humidity are fatal to even the most elaborate hairstyles.

A frequent solution to this problem is the use of styling gels, hair foams, hair waxes, hairsprays, fixing gels, and the like. These types of products, however, are often not effective, and most tend to leave the hair with a sticky and unnatural feeling. Therefore, a truly effective product that allows hair styles to withstand adverse environmental conditions and leave the hair feeling soft and natural (i.e., have good sensory attributes) is currently needed.

SUMMARY

Previously, we identified that waterborne polyurethanes possessing certain properties were found to produce cosmetic compositions having enhanced hold, high humidity curl retention, and/or positive sensory attributes. See WO 2017/155906, the contents of which are incorporated herein by reference. Here, it has now been found that these properties extend to other chemistries, each having similar affirmative results, thereby increasing the amount and versatility of hair styling products available to the consumer.

Provided herein, therefore, are hair styling compositions comprising one or more non-polyurethane or non-polyurethane urea based polymers having a Young's modulus above 150 MPa; an elongation at break of from about 15% to about 300%; and a moisture uptake of less than 10%.

The compositions described herein were shown to provide outstanding results in vivo. See e.g., FIG. 3 which shows a direct comparison between an acrylates copolymer composition having the disclosed Young's modulus, elongation at break, and moisture uptake and an acrylates copolymer composition falling outside of the scope of these properties. As shown by the results, excellent retention of curl shape and definition was achieved with the inventive compositions even under high humidity conditions.

DETAILED DESCRIPTION

1. Definitions

A "hair style" product or "hair style" composition is one that can be used to alter the texture and/or shape of the hair, or to hold the hair in a particular style e.g., a curl, wave, feather, spike, etc. Types of hair style products include, but are not limited to, gels, waxes, mousses, pomades, hair sprays, hair volumizers, and the like.

As used herein, a "non-polyurethane polymer" means a polymer which does not comprise organic units joined by a —O—C(O)—NH— unit.

As used herein, a "non-polyurethane urea based" polymer means a polymer which does not comprise organic units joined by a —O—C(O)—NH— and a —NH—C(O)—NH- linkage.

"Young's modulus (or the modulus of elasticity, tensile modulus)" is a measure of the stiffness of a solid polymer film. Young's modulus, E, can be calculated by dividing the tensile stress by the extensional strain in the elastic (initial, linear) portion of the stress-strain curve. The Young's modulus of the disclosed polymers can be determined by a protocol defined to measure mechanical properties, and is developed in reference to ASTM D638, ASTM D412, test guidelines as described below in Example 2.

The "elongation at break (also known as fracture strain, ultimate elongation)" is the ratio between changed length and initial length after breakage of a solid polymer film. The elongation at break of the disclosed polymers can be determined by a protocol defined to measure mechanical properties, and is developed in reference to ASTM D638, ASTM D412, test guidelines as described below in Example 2.

The "moisture uptake" is the measure of water adsorbed by a solid polymer film. The method for determining the moisture uptake of the disclosed polymers is provided in Example 3.

The "sensory score" is determined by the performance of the hair fixative. In particular, the tress with the composition applied is blow dried for 90 seconds. The tresses are prepared in duplicate and blinded randomly and evaluated for natural feeling and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes.

As used herein, "polyacrylates" refer to polymers formed from acrylic acid ($CH_2$=CHCOOH). Polyacrylates include, but are not limited to, polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, 2-ethylacrylic acid, and (2-trifluoromehtyl)acrylic acid, and combinations thereof.

As used herein, "polystyrenes" refer to aromatic polymers formed from styrene ($C_6H_5CH=CH_2$). Polystyrenes include, but are not limited to, polystyrene sulfonate, polystyrene phosphonate, polystyrene carboxylate, and (aminomethyl)polystyrene, hydroxymethylpolystyrene, and combinations thereof.

As used herein, "polyacrylamides" refer to polymers formed from acrylamide subunits ($CH_2CHCONH_2$). Polyacrylamides include, but are not limited to, acrylamide, methacrylamide, octylacrylamide, t-Butylacrylamide, N-isopropyl acrylamide, Poly(2-acrylamido-2-methyl-1-propanesulfonic acid, and Poly(N,N-dimethylacrylamide), and combinations thereof.

As used herein, "polyvinyl polymers" refer to polymers which are derived from vinyl monomers ($CHR=CHR$). Polyvinyl polymers, include, but are not limited to polyvinyl acetate, polyvinylpyrrolidone, polyvinyl neodecanoate, polyvinyl imidazole, polyvinyl alcohol, polyvinyl chloride, and polyvinylcaprolactam, and combinations thereof.

As used herein, "polyquaterniums" refer to polymers which contain a quaternary ammonium center. Polyquaterniums include, but are not limited to, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-42, Polyquaternium-43, Polyquaternium-44, Polyquaternium-45, Polyquaternium-46, Polyquaternium-47, Polyquaternium-55, and Polyquaternium-69, and combinations thereof.

As used herein, "polyamides" refer to polymers which contain repeating amide bonds. Polyamides include aliphatic polyamides, polyphthalamides, and aramides.

As used herein, "polyimides" refer to polymers which are formed from imide monomers. Examples include poly (amide-imide) and polyimide As used herein, "polysaccharides" refer to long chain monosaccharide units bound by glycosidic linkages. Examples include starch, glycogen, cellulose, larch gum, alginic acid, chitin, chitosan, argarose, carrageenan, hyaluronic acid, dextran, dextrin, gellan gum, pullulan, and pectin, and combinations thereof.

2. Young's Modulus, Elongation at Break, and Moisture Uptake

The combination of mechanical properties described herein include the Young's modulus (e.g., above 150 MPa), the elongation at break (e.g., from about 15% to about 300%), and hydrophobicity (moisture uptake, e.g., less than 10%).

In one aspect, the Young's modulus of the disclosed non-polyurethane or non-polyurethane urea based polymers should be above about 150 MPa. For example, the Young's modulus of the disclosed one or more non-polyurethane or non-polyurethane urea based polymers may be above about 160 MPa, above about 170 MPa, above about 180 MPa, above about 190 MPa, above about 200 MPa, above about 210 MPa, above about 220 MPa, above about 230 MPa, above about 240 MPa, above about 250 MPa, above about 260 MPa, above about 270 MPa, above about 280 MPa, above about 290 MPa, above about 300 MPa, above about 310 MPa, above about 320 MPa, above about 330 MPa, above about 340 MPa, above about 350 MPa, above about 360 MPa, above about 370 MPa, above about 380 MPa, above about 390 MPa, above about 400 MPa, above about 410 MPa, above about 420 MPa, above about 430 MPa, above about 440 MPa, above about 450 MPa, above about 460 MPa, above about 470 MPa, above about 480 MPa, above about 490 MPa, above about 500 MPa, above about 510 MPa, above about 520 MPa, above about 530 MPa, above about 540 MPa, or above 550 MPa. In other aspects, the Young's modulus of the non-polyurethane or non-polyurethane urea based polymers should be between about 150 MPa and about 500 MPa. For example, the Young's modulus of the non-polyurethane or non-polyurethane urea based polymers may be between about 150 MPa and about 300 MPa, between about 150 MPa and about 290 MPa, between about 150 MPa and about 225 MPa, between about 200 MPa and about 300 MPa, between about 240 MPa and about 290 MPa, or between about 150 MPa and about 200 MPa.

In one aspect, the elongation at break of the disclosed non-polyurethane or non-polyurethane urea based polymers should be from about 15% to about 300%. For example, the elongation at break of the disclosed non-polyurethane or non-polyurethane urea based polymers may be from about 20% to about 300%, from about 25% to about 300%, from about 40% to about 280%, from about 100% to about 280%, from about 100% to about 250%, from about 150% to about 250%, from about 200% to about 250%, from about 210% to about 250%, about 30 to about 150%, from about 15% to about 150%, from about 150% to about 300%, from about 50 to about 250%; from about 75 to about 225%, or from about 100 to about 200%. In other aspects, the disclosed non-polyurethane or non-polyurethane urea based polymers may be from about 15% to about 100%, from about 20% to about 100%, or from about 50% to about 100%. The elongation break may be optionally combined with one or more of the Young's modulus values described in the paragraph above or any one of the Young's modulus values described in the remainder of the disclosure.

In one aspect, the moisture uptake of the disclosed non-polyurethane or non-polyurethane urea based polymers should be less than about 10%. For example, the moisture uptake of the disclosed non-polyurethane or non-polyurethane urea based polymers may be less than about 9.5%, less than about 9%, less than about 8.5%, less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, less than about 0.5%, or is about 0%. In one aspect, the moisture uptake of the disclosed non-polyurethane or non-polyurethane urea based polymers should be from about 0% to about 10%. For example, the moisture uptake may be from about 0% to about 8%, from about 2% to about 8%, or from about 3% to about 7%. The moisture uptake may be optionally combined with one or more of the Young's modulus values, one or more of the elongation break values, or both as described in the paragraphs above or in the remainder of the disclosure.

As shown in the Exemplification section below, the disclosed non-polyurethane or non-polyurethane urea based polymers have improved performance (e.g., enhanced hold, high humidity curl retention, improved stylability, natural curl enhancement, and minimization of flyaways).

Additional Indicators

In addition to the Young's modulus, elongation at break, and moisture uptake, other indicators may be used to identify the capability of the disclosed non-polyurethane or non-polyurethane urea based polymers to provide long lasting, moisture-resistant hold hair product with favorable sensory attributes. Such indicators include e.g., change in tress length and sensory score.

Thus, in certain aspects, the disclosed non-polyurethane or non-polyurethane urea based polymers may be selected such that the composition, after being applied to a curled hair tress and dried thereon, provides less than about 80% change in tress length as measured by the high humidity mechanical stress test. For example, the disclosed non-polyurethane or non-polyurethane urea based polymers may be selected such that the composition, after being applied to a curled hair tress and dried thereon, provides less than about 75%, about 70%, about 65%, about 60%, about 55%, about 50%, about 45%, about 40%, about 35%, about 30%, about 25%, about 20%, about 15%, about 10%, about 5%, or about 0% change in tress length as measured by the high humidity mechanical stress test. The change in tress length as described herein may also be combined with any one of the Young's modulus values, elongation at break values, and moisture uptake values described above and herein.

In other aspects, the disclosed non-polyurethane or non-polyurethane urea based polymers may be selected such that the composition, after being applied to a hair tress and dried thereon, provides a sensory score of at least about 0. For example, the disclosed non-polyurethane or non-polyurethane urea based polymers in the disclosed compositions may be selected such that the composition, after being applied to a hair tress and dried thereon, provides a sensory score of at least about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5. The sensory score feature as described herein may also be combined with any one of the change in tress length values, the Young's modulus values, the elongation at break values, and the moisture uptake values described above and herein.

3. Compositions

Provided herein are hair styling compositions comprising one or more non-polyurethane or non-polyurethane urea based polymers having a Young's modulus above 150 MPa; an elongation at break of from about 15% to about 300%; and a moisture uptake of less than 10%.

In one aspect, the one or more polymers in the disclosed compositions are selected from polyacrylates, polystyrenes, polyacrylamides, polyacrylic acids, polyvinyl polymers, polyquaterniums, polyimides, polyamides, and polysaccharides, or a combination thereof.

In one aspect, the one or more polymers in the disclosed compositions are a combination of polyacrylates and polystyrenes. In one aspect, the weight ratio of polyacrylates to polystyrenes in the disclosed compositions is 1:99 to 99:1. In another aspect, the one or more polymers in the disclosed compositions are a combination of polyacrylates and polystyrenes wherein the polystyrenes are selected from polystyrene sulfonate, polystyrene phosphonate, polystyrene carboxylate, or a combination thereof, and wherein the weight ratios are expressed above. In yet another aspect, the one or more polymers in the disclosed compositions are a combination of polyacrylates and polystyrenes wherein the polystyrenes are selected from polystyrene sulfonate, polystyrene phosphonate, polystyrene carboxylate, or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polyacrylamides. In one aspect, the weight ratio of polyacrylates to polyacrylamides in the disclosed compositions is 1:99 to 99:1. In another aspect, the one or more polymers in the disclosed compositions are a combination of polyacrylates and polyacrylamides, wherein the polyacrylamides are selected from acrylamide, methacrylamide, octylacrylamide, t-Butylacrylamide, N-isopropyl acrylamide or a combination thereof, and wherein the weight ratios are expressed above. In yet another aspect, the one or more polymers in the disclosed compositions are a combination of polyacrylates and polyacrylamides, wherein the polyacrylamides are selected from acrylamide, methacrylamide, octylacrylamide, t-Butylacrylamide, N-isopropyl acrylamide or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polyvinyl polymers. In one aspect, the weight ratio of polyacrylates to polyvinyl polymers in the disclosed compositions is 1:99 to 99:1. In another aspect, the one or more polymers in the disclosed compositions are a combination of polyacrylates and polyvinyl polymers, wherein the polyvinyl polymers are selected from polyvinyl acetate, polyvinylpyrrolidone, polyvinyl neodecanoate, polyvinyl imidazole, and polyvinylcaprolactam, or a combination thereof, and wherein the weight ratios are expressed above. In yet another aspect, the one or more polymers in the disclosed compositions are a combination of polyacrylates and polyvinyl polymers, wherein the polyvinyl polymers are selected from polyvinyl acetate, polyvinylpyrrolidone, polyvinyl neodecanoate, polyvinyl imidazole, and polyvinylcaprolactam, or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polyquaterniums. In one aspect, the weight ratio of polyacrylates to polyquaterniums in the disclosed compositions is 1:99 to 99:1. In another aspect, the one or more polymers in the disclosed compositions are a combination of polyacrylates and polyquaterniums, wherein the polyquaterniums are selected from Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-42, Polyquaternium-43, Polyquaternium-44, Polyquaternium-45, Polyquaternium-46, Polyquaternium-47, Polyquaternium-55, and Polyquaternium-69, or a combination thereof. In yet another aspect, the one or more polymers in the disclosed compositions are a combination of polyacrylates and polyquaterniums, wherein the polyquaterniums are selected from Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-42, Polyquaternium-43, Polyquaternium-44, Polyquaternium-45, Polyquaternium-46, Polyquaternium-47, Polyquaternium-55, and Polyquaternium-69, or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polyamides. In one aspect, the polyamides can be aliphatic polyamides, polyphthalamides, or aramides. In one aspect, the weight ratio of polyacrylates to polyamides in the disclosed compositions is 1:99 to 99:1. In one aspect, the one or more polymers in the disclosed compositions are a combination of polyacrylates and polyamides, wherein the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polyimides. In one aspect, the weight ratio of polyacrylates to polyimides in the disclosed compositions is 1:99 to 99:1. In one aspect, the one or more polymers in the disclosed compositions are a combination of polyacrylates and polyimides, wherein the polyimides are selected from poly(amide-imide) and polyimide, or a combination thereof. In one aspect, the one or more polymers in the disclosed compositions are a combination of polyacrylates and polyimides, wherein the polyimides are selected from poly(amide-imide) and polyimide, or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed compositions are a combination of polyacrylates and polysaccharides. In one aspect, the weight ratio of polyacrylates to polysaccharides in the disclosed compositions is 1:99 to 99:1. In another aspect, the one or more polymers in the disclosed compositions are a combination of polyacrylates and polysaccharides, wherein the polysaccharides are selected from starch, glycogen, cellulose, larch gum, alginic acid, chitin, chitosan, argarose, carrageenan, hyaluronic acid, dextran, dextrin, gellan gum, pullulan, and pectin, or a combination thereof. In yet another aspect, the one or more polymers in the disclosed compositions are a combination of polyacrylates and polysaccharides, wherein the polysaccharides are selected from starch, glycogen, cellulose, larch gum, alginic acid, chitin, chitosan, argarose, carrageenan, hyaluronic acid, dextran, dextrin, gellan gum, pullulan, and pectin, or a combination thereof and the polyacrylates are selected from polymethacrylate, tert-butylaminoethyl methacrylate, poly(benzyl methacrylate), poly(butyl methacrylate), poly(cyclohexyl methacrylate), poly(dodecylmethacrylate), poly(2-ethoxyethyl methacrylate), poly(ethyl methacrylate), poly(hexyl methacrylate), poly(2-hydroxyethyl methacrylate), poly(isobutyl methacrylate), poly(isopropyl methacrylate), poly(methyl methacrylate), poly(octadecyl methacrylate), poly(octyl methacrylate), poly(phenyl methacrylate), poly(propyl methacrylate), poly(2-chloroethyl methacrylate), Ammonium Polyacrylate, Potassium Aluminum Polyacrylate, Potassium Polyacrylate, Sodium Polyacrylate, or a combination thereof, and wherein the weight ratios are expressed above.

In one aspect, the one or more polymers in the disclosed composition are selected from Ammonium Acrylate Copolymer, Ammonium Vinyl Acetate/Acrylate Copolymer, Sodium Acrylate Copolymer, Ethylene/Acrylic Acid Copolymer, Ethylene/Calcium Acrylate Copolymer, Ethylene/Magnesium Acrylate Copolymer, Ethylene/Sodium Acrylate Copolymer, Ethylene/Zinc Acrylate Copolymer, Ethylene/Acrylic Acid/Vinyl Acetate Copolymer, Acrylates/Vinyl Acetate Copolymer, Acrylate/Vinyl Acetate Copolymer, Steareth-10 Allyl Ether/Acrylate Copolymer, Acrylate/Steareth-50 Acrylate Copolymer, Acrylate/Steareth-20 Methacrylate Copolymer, Acrylate/Ammonium Methacrylate Copolymer, Styrene/Acrylate Copolymer, Styrene/Acrylate/Ammonium Methacrylate Copolymer, Ammonium Styrene/Acrylate Copolymer, Sodium Styrene/Acrylate Copolymer, Acrylate/Hydroxyester Acrylate Copolymer, Methacryloyl Ethyl Betaine/Acrylate Copolymer, Lauryl Acrylate/Vinyl Acetate Copolymer, Vinyl Acetate/Butyl Maleate/Isobornyl Acrylate Copolymer, Ethylene/Methacrylate Copolymer, Vinyl Caprolactam/Vinyl Pyrrolidone/Dimethylaminoethyl Methacrylate Copolymer, Sodium Acrylate/Acrolein Copolymer, Vinyl Pyrrolidone/Dimethylaminoethylmethacrylate Copolymer, Aminomethyl Propanol-Acrylate Copolymer, Polyacrylic Acid, Ammonium Polyacrylate, Potassium Aluminum Polyacrylate, Potassium Polyacrylate, Sodium Polyacrylate, Octyacrylamide/Acrylate/Butylaminoethyl Methacrylate Copolymer, Acrylates/C1-2 Succinate/Hydroxyacrylate Copolymer, Acrylate/Methacrylamide Copolymer, Acrylate/t-Butylacrylamide Copolymer, Acrylate/Octylacrylamide Copolymer, Vinyl Acetate/Crotonate/Vinyl Neodecanoate Copolymer, Polyvinylpyrrolidone/Vinyl acetate Copolymer, Vinyl Pyrrolidone/Methacrylamide/Vinyl Imidazole Copolymer, Acrylamide/Sodium Acryloyldimethyltaurate/Acrylic Acid Copolymer, Poly(benzyl methacrylate), Poly(butyl methacrylate), Poly(cyclohexyl methacrylate), Poly(dodecylmethacrylate), Poly(2-ethoxyethyl methacrylate), Poly(ethyl methacrylate), Poly(hexyl methacrylate), Poly(2-hydroxyethyl methacrylate), Poly(isobutyl methacrylate), Poly(isopropyl methacrylate), Poly(methyl methacrylate), Poly(octadecyl methacrylate), Poly(octyl methacrylate), Poly(phenyl methacrylate), Poly(propyl methacrylate), Poly(2-chloroethyl methacrylate), Polystyrene sulfonate, Polystyrene phosphonate, Polystyrene carboxylate, acrylate/octylacrylamide copolymers, polyvinylcaprolactam polymers, octylacrylamide/acrylate/butylaminoethyl methacrylate copolymers, polyquaternium-69 polymers, and Vinyl Pyrrolidone/Methacrylamide/Vinyl Imidazole copolymers, N-isopropylacrylamide. In another aspect, the one or more polymers in the disclosed composition are selected from acrylate copolymer, acrylate/octylacrylamide copolymer, polyvinylcaprolactam polymer, octylacrylamide/acrylate/butylaminoethyl methacrylate copolymer, polyquaternium-69 polymer, and Vinyl Pyrrolidone/Methacrylamide/Vinyl Imidazole copolymer.

In one aspect, the disclosed composition comprises a 1:10 to 15:1 ratio by weight of acrylates copolymer:corn starch modified; a 1:10 to 20:1 ratio by weight of acrylates copolymer:acrylates/octylacrylamide copolymer; a 1:2 to 50:1 ratio by weight of acrylates copolymer:polyvinylcaprolactam; a 1:1 to 100:1 ratio by weight of acrylates copolymer:octylacrylamide/acrylates/butylaminoethyl methacrylate copolymer; a 1:10 to 20:1 ratio by weight of acrylates copolymer:polyquaternium-69; or a 1:10 to 20:1 ratio by weight of acrylates copolymer:vinyl pyrrolidone/methacrylamide/vinyl imidazole copolymer. In another aspect, the disclosed composition comprises a 1.5:1 ratio by weight of acrylates copolymer:corn starch modified; a 1.9:1 ratio by weight of acrylates copolymer:acrylates/octylacrylamide copolymer; a 4:1 ratio by weight of acrylates copolymer:polyvinylcaprolactam; a 1.5:1 ratio by weight of acrylates copolymer:octylacrylamide/acrylates/butylaminoethyl methacrylate copolymer; a 2.3:1 ratio by weight of acrylates copolymer:polyquaternium-69; or a 2.0:1 ratio by weight of acrylates copolymer:vinyl pyrrolidone/methacrylamide/vinyl imidazole copolymer.

In some aspects, the compositions described herein are aqueous solutions or aqueous dispersions. In one aspect, the aqueous solutions or aqueous dispersions further comprise ethanol.

In some aspects, the disclosed compositions are neutralized with an alkaline neutralizer. In one aspect, the disclosed compositions are neutralized with triethanolamine, 2-amino-2-methyl-1-propanol, ammonium hydroxide, potassium hydroxide, or long chain alkyl amines, such as triisopropyl amine, dimethyl stearamine, and dimethyl hydrogenated tallow amine.

In other aspects, when the disclosed composition comprises one or more non-polyurethane or non-polyurethane urea based polymers having carboxylic acid residues, about 70% to 100% of those carboxylic acid residues may be neutralized e.g., with an alkaline neutralizer as described herein.

In one aspect, the disclosed compositions are applied to the hair with water.

In one aspect, the disclosed compositions, when applied to the hair, change the texture and appearance.

In one aspect, the disclosed compositions, when applied to the hair, improve hold, i.e. hair that is formed into a given curl or style retains that curl or style over time.

In one aspect, the disclosed compositions, when applied to the hair, provide sufficient stylability, i.e. the composition applied to hair supplies sufficient rigidity and flexibility to form and maintain a style.

In one aspect, the disclosed compositions, when applied to the hair, minimize flyaways, i.e. there are minimal individual hair fibers that do not conform to the given curl or style.

In one aspect, the disclosed compositions, when applied to the hair, preserve curl shape, i.e. hair that is formed into a given curl retains that curl over time.

In one aspect, the disclosed compositions, when applied to the hair, provides natural curl enhancement, i.e. hair that naturally tends to curl displays a more defined and less diffused curl pattern.

The compositions described herein may further comprise an antioxidant. Antioxidants that may be suitable with the compositions described herein include, but are not limited to, acai oil, alpha lipoic acid, green and white tea, retinol, vitamin C, Vitamin E, butylated hydroxytoluene, butylated hydroxyanisole, coenzyme Q10 (Co Q-10), isoflavones, polyphenols, curcumin, turmeric, pomegranate, rosemary, glutathione, selenium, and zinc.

EXEMPLIFICATION

Example 1. Chemical Compositions and Properties

Compositions were formulated by water or mixture of water and ethanol. The ratio of constituents in the final blend together with the properties are shown in Table 1.

made to several commercially available polyurethane products. The Young's modulus and the elongation at break can be determined by a protocol defined to measure mechanical properties is developed in compliance with ASTM D638, ASTM D412, test guidelines. In particular, the following protocol can be used to determine the Young's modulus and elongation at break (or ultimate elongation) of dry film of polyurethanes. Testing requires approximately 10-20 min per sample to complete.

TABLE 1

| No. | Material Name | Material 1 | Material 2 | Material 1:2 ratio | Young's Modulus (MPa) | Elongation at Break (%) | Moisture Uptake (%) |
|---|---|---|---|---|---|---|---|
| 1 | AC2 | Acrylates Copolymer | Acrylates Copolymer | 1.6:1 | 164 ± 10 | 32 ± 11 | 2.60 ± 0.09 |
| 2 | ACCSM | Acrylates Copolymer | Corn Starch Modified | 1.5:1 | 159 ± 12 | 33 ± 13 | 4.49 ± 0.74 |
| 3 | AOC2 | Acrylates Copolymer | Acrylates/Octylacrylamide Copolymer | 1.9:1 | 186 ± 9 | 22 ± 6 | 8.99 ± 0.12 |
| 4 | ACPV | Acrylates Copolymer | Polyvinylcaprolactam | 4:1 | 185 ± 12 | 79 ± 28 | 5.42 ± 0.20 |
| 5 | AOBMC | Acrylates Copolymer | Octylacrylamide/Acrylates/Butylaminoethyl Methacrylate Copolymer | 1.5:1 | 266 ± 20 | 16 ± 4 | 10.23 ± 0.52 |
| 6 | ACPQ | Acrylates Copolymer | Polyquaternium-69 | 2.3:1 | 266 ± 13 | 23 ± 5 | 9.84 ± 0.42 |
| 7 | AVPMVIC | Acrylates Copolymer | VP/Methacrylamide/Vinyl Imidazole Copolymer | 2.0:1 | 205 ± 16 | 47 ± 11 | 11.67 ± 0.17 |

Table 2 below shows the processing information related to the compositional breakdown of the materials.

TABLE 2

| Material Name | Conc. | Solvents | Neutralization |
|---|---|---|---|
| Acrylates Copolymer | 10% | Water | N/A |
| Corn Starch Modified | 5% | Water | N/A |
| Acrylates/Octylacrylamide Copolymer | 10% | Water:Ethanol = 2:1 (w/w) | 100% |
| Polyvinylcaprolactam | 10% | Water | N/A |
| Octylacrylamide/Acrylates/Butylaminoethyl Methacrylate Copolymer | 10% | Water:Ethanol = 2:1 (w/w) | 100% |
| Polyquaternium-69 | 10% | Water | N/A |
| VP/Methacrylamide/Vinyl Imidazole Copolymer | 10% | Water | N/A |

Example 2. Mechanical Performance

The Young's modulus is a measure of the ability of a material to withstand changes in length when under uniaxial tension or compression. A higher Young's modulus typically indicates that the material is more rigid. The elongation at break, also known as fracture strain, is the ratio between changed length and initial length after breakage of the test specimen. A higher elongation at break expresses the capability of a material to resist fracture. For a composition applied to hair to hold the shape of the hair, the Young's modulus and elongation at break of the composition should be such that the composition provides rigidity to the hair but is not brittle.

A comparison of Young's modulus and the elongation at break for the some of the polyurethanes disclosed herein was Materials:
>25 g polymer aqueous dispersion
1 clean rectangular mold (2 mm×20 mm×45 mm) grooved on Teflon sheet per sample
1 clean razor blade
Scotch tape
Universal Testing Machine mounted with extension grip geometry Sample Preparation:
1. Prepare 25 g of 10 wt % polymer solution from their respective stock solution.
2. Apply 2.5 mL prepared solution in each mold (2 mm×20 mm×45 mm) and allow drying for 2 days to give polymer film.
3. After it dries out, use a spatula to remove film from the mold.
4. Use the razor blade to cut corners and get film with around 15 mm width and around 150-300 micron thickness. Make sure that the film is free of air bubbles.
5. Label the test film.
6. Cut four pieces of tape (20 mm) per sample and adhere them to both sides of the specimen strip and make a dog-bone shaped sample to improve hold of sample in grip. Store the prepared test films in desiccators for 1-2 hour to fully dry them. Take one sample out of desiccators at a time for testing.

Sample Testing
1. Balance the load registering on the universal testing machine so that it reads 0 Newtons.
2. Use calipers to set a distance of 20 mm between the top and bottom extension grip geometries.
3. Mount a sample in the extension grips and secure tightly, ensuring that the scotch tape is not visible, and that the sample is as close to vertical as possible in both vertical planes.
4. Stretch the sample slightly, by separating the geometries until a force of 2-5 N is registered.

5. Begin a tensile testing run on the universal testing machine at a speed of 100 mm/minute, stopping the test upon sample fracture.
6. Elongation at break is calculated at the elongation at which the material fractures.
7. Young's modulus is calculated as the modulus during the initial, elastic portion of deformation by calculating the slope of a linear fit to that region with an R value >0.99.
   a) low modulus and high elongation, which leads to inferior curl hold (e.g., hold is temporary, transient, or short-lived) or
   b) high modulus and low elongation, which leads to a brittle material with low performance (e.g., resin is brittle or fractures) after manipulation.

Example 3. Hydrophobicity/Water Uptake of Polyurethane

The following protocol can be used to determine moisture uptake ability of the disclosed polymers under high humid environment. Test requires about 2-3 days per sample set to complete Materials >15 g polymer solution 1 clean cell culture petri dish (60 mm dia×15 mm H) per sample Humidity chamber with flexibility to control temperature and relative humidity (RH)

Sample Testing

1. Prepare 15 g of 10 wt % polymer solution from respective stock solution.
2. Label cell culture petri dishes for each sample and measure their empty weight ($W_{pd}$).
3. Apply 4 mL prepared solution in each petri dish (3 samples per polymer and allow to equilibrate for 20 hours at 25° C. and 50% RH in humidity chamber.
4. After equilibration, measure and record sample weight ($W_f$).
5. Place the samples to humidity chamber at 25° C. and 90% RH and allow equilibration to high humidity for 20 hours.
6. Measure and record final sample weight (W).

Sample Analysis

Calculate % moisture uptake using the following equation:

$$\% \text{ moisture uptake} = \left[\frac{((Wf - Wpd) - (Wi - Wpd))}{(Wi - Wpd)}\right] \times 100\%$$

Example 4. Tress Testing

Systematic in vitro performance testing on the disclosed compositions and those without the target mechanical properties and water uptake (Table 3) were tested. In all in vitro testing, materials were applied at 3 wt % solids concentration. Results show that materials with target properties yield excellent high humidity curl retention compared to the materials without the optimal properties.

TABLE 3

| Material Name | Material Description | Materials Properties |
|---|---|---|
| P48 | Polyurethane-48 | Suboptimal Properties: |
| AC1 | Acrylates Copolymer | Outside of the optimal |
| AOC1 | Acrylates/Octylacrylamide Copolymer | properties |
| PV | Polyvinylcaprolactam | |
| AC2 | Acrylates Copolymer | Optimal Properties: |
| ACCSM | Acrylates Copolymer/Corn Starch Modified | Young's Modulus: >150 MPa Elongation at Break: 15-300% |
| AOC2 | Acrylates Copolymer/Acrylates/Octylacrylamide Copolymer | |
| ACPV | Acrylates Copolymer/Polyvinylcaprolactam | Water Uptake: <10% |
| AOBMC | Acrylates Copolymer/Octylacrylamide/Acrylates/Butylaminoethyl Methacrylate Copolymer | |
| WBPU | Waterborne Polyurethane | |

Figure 1:
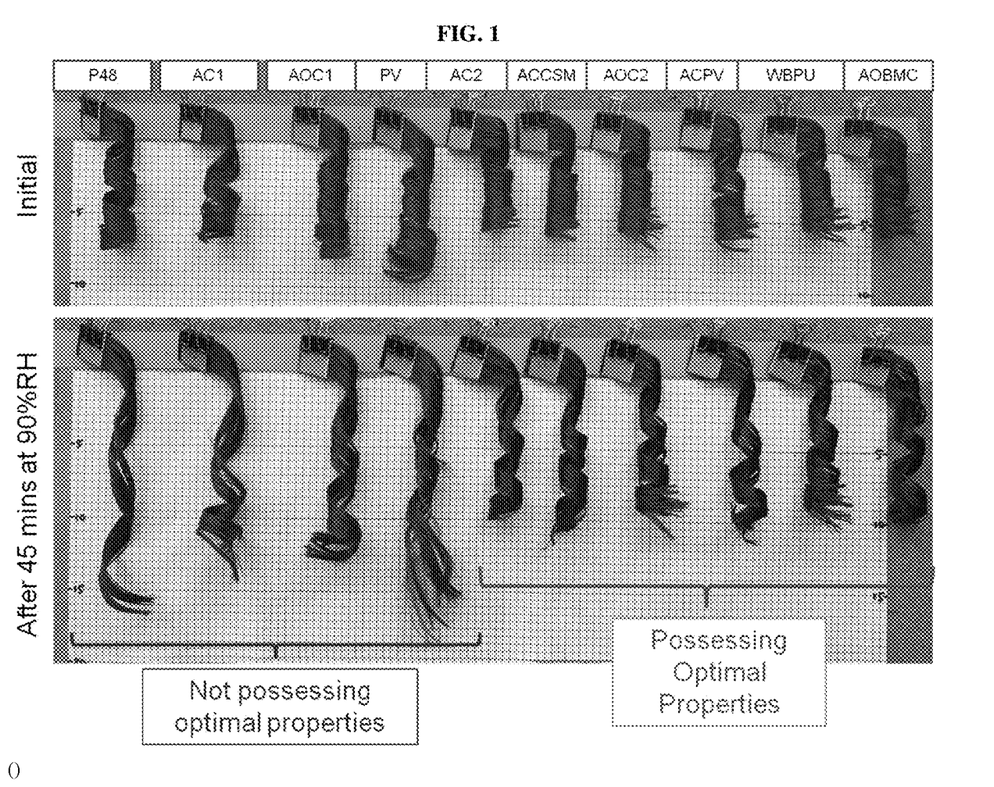
FIG. 1 shows an example of hair tresses before and after high humidity test styled using compositions described herein and those falling outside the scope of the disclosed Young's modulus, elongation at break, and moisture uptake.

As shown by FIG. 1, the inventive compositions having the disclosed Young's modulus, elongation at break, and water uptake, showed excellent high humidity curl retention-curls stay intact and do not drop dramatically. In contrast, curls where the materials with suboptimal properties were applied dropped dramatically after equilibrium at 90% relative humidity. A summary of the in vitro tests conducted is given in Table 4.

TABLE 4

| Materials | Initial Curl Length Range (cm) | Final Curl Length Range (cm) | Delta L Range (Change in Curl Length, cm) |
|---|---|---|---|
| With optimal properties | 5-7 | 8-10 | 2-5 |
| Without optimal properties | 6-9 | 10-14 | 4-8 |

Example 5. In Vivo Performance

Figure 2:
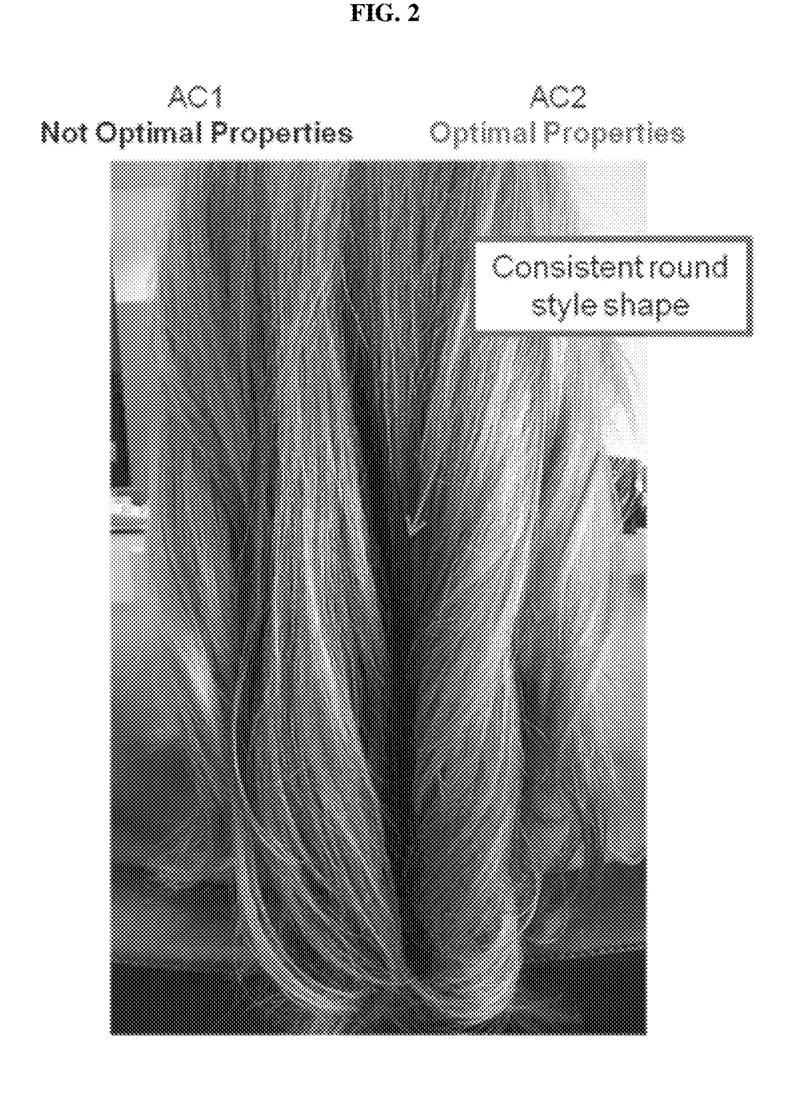
FIG. 2 shows in vivo testing showing more volume and a consistent, round style to the hair after blowout using a composition described herein compared with a composition falling outside the scope of the disclosed Young's modulus, elongation at break, and moisture uptake.

To validate the in vitro results, and to assess performance under normal hair care product use conditions, systematic in vivo performance testing on inventive and non-inventive compositions (i.e., those not having the disclosed Young's modulus, elongation at break, and water uptake) were conducted. In in vivo testing, materials were applied at 3 wt % solids concentration. Results showed that materials with target properties have excellent style hold as opposed to materials without the combination of optimal properties, which do not perform as well. FIG. 2 shows an example of hairstyle in which the left side of the head has been treated with Acrylates Copolymer not having the disclosed Young's modulus, elongation at break, and water uptake, and the right side of the head has been treated with Acrylates Copolymer which possesses the target properties. The material possessing the disclosed Young's modulus, elongation at break, and water uptake (right) provides more volume and a consistent, rounded style to the hair after the blowout, which is very desirable. The material not outside of the scope of these properties provides a limp style with less volume. FIG. 2 also shows that the inventive composition (right) yields more aligned hair with minimal flyaway fibers, and is thus more desirable than the hair styled using material without the described combination of properties (left).

Figure 3:
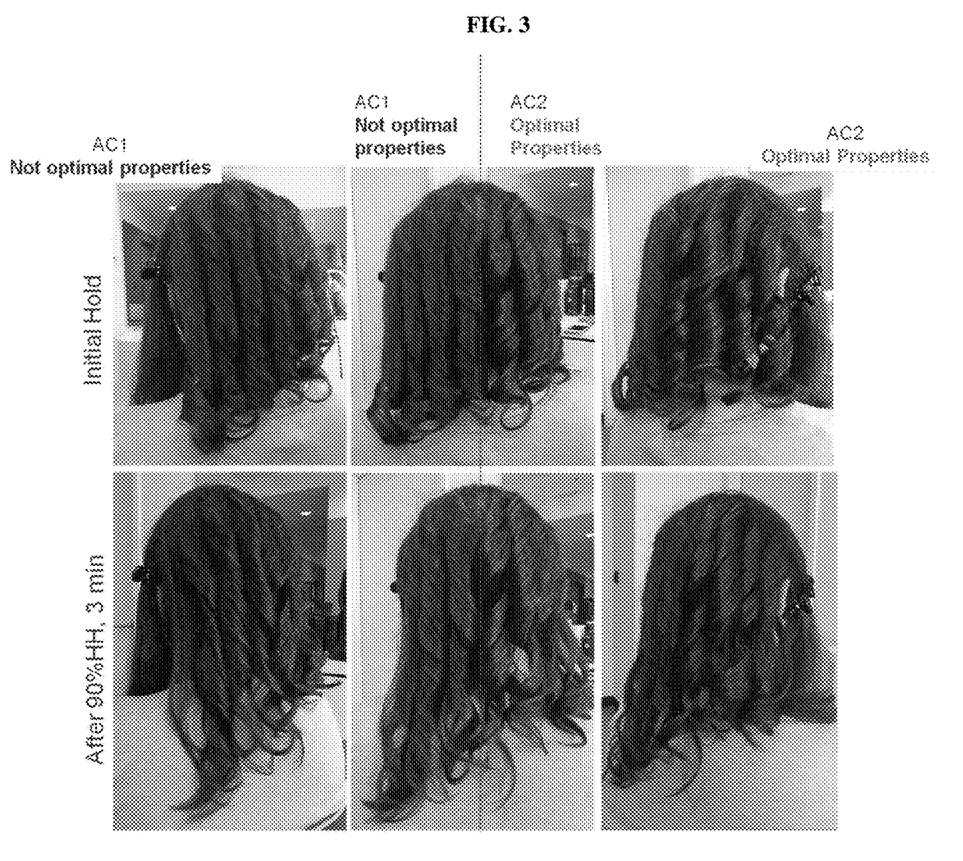
FIG. 3 shows in vivo testing showing better initial hold and high humidity curl retention using a composition described herein compared with a composition falling outside the scope of the disclosed Young's modulus, elongation at break, and moisture uptake.

FIG. 3 shows an example of curl retention test after exposure to high humidity. The left side of the head was treated with Acrylates Copolymer outside of the target zone and the right side of the head has been treated with Acrylate Copolymer having the disclosed Young's modulus, elongation at break, and water uptake values. The inventive composition (right) showed better initial hold and significantly better curl retention after exposure to high humidity. The composition falling outside the scope of the target properties (left) elicited dramatic drop in curl length after exposure to high humidity.

These results support the finding that hair styling compositions comprising one or more non-polyurethane or non-polyurethane urea based polymers having a Young's modulus above 150 MPa; an elongation at break of from about 15% to about 300%; and a moisture uptake of less than 10%, produce superior hold and retain curly shape under environmentally unfriendly conditions such as e.g., high humidity.

Example 5. Sensory Performance

The sensory properties of hair treated with various materials was evaluated by blinded, trained sensory evaluators for properties such as fiber alignment, hair softness, and overall appearance on a scale of −2 to +2.

Material not having the disclosed properties (Acrylates Copolymer) was modified with four different materials (Acrylates/Octylacrylamide Copolymer, Corn Starch Modified, Acrylates Copolymer, or Octylacrylamides/Acrylates/Butylaminoethyl Methacrylate Copolymer), resulting in four inventive compositions having the disclosed Young's modulus, elongation at break, and water uptake. When hair treated with these materials was scored by the sensory evaluators, in 75% of cases the materials possessing optimal properties had improved sensory properties compared to materials not possessing optimal properties (Table 5). In addition, when a material outside of the target property zone that has a good sensory score (such as Acrylates Copolymer or Corn Starch Modified) is optimized to meet the target properties, their sensory scores are not significantly impacted.

TABLE 5

| Material | Possessing Optimal Properties | Sensory Score[a] |
| --- | --- | --- |
| Acrylates Copolymer | X | −0.75 |
| Mixture of Materials | Possessing Optimal Properties | Sensory Score |
| Acrylates Copolymer:Acrylates/Octylacrylamide Copolymer | √ | −0.42 |
| Acrylates Copolymer: Corn Starch Modified | √ | +0.46 |
| Acrylates Copolymer: Acrylates Copolymer | √ | +1.25 |
| Acrylates Copolymer: Octylacrylamides/Acrylates/Butylaminoethyl Methacrylate Copolymer | √ | −1.2 |

[a]Scores are assigned by blinded, trained sensory evaluators on a scale of −2 to +2.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A hair styling composition consisting essentially of:
   a 1.5:1 ratio by weight of acrylates copolymer:corn starch modified;
   a 1:10 to 20:1 ratio by weight of acrylates copolymer: acrylates/octylacrylamide copolymer;
   a 1:2 to 50:1 ratio by weight of acrylates copolymer: polyvinylcaprolactam;
   a 1:1 to 100:1 ratio by weight of acrylates copolymer: octylacrylamide/acrylates/butylaminoethyl methacrylate copolymer;
   a 1:10 to 20:1 ratio by weight of acrylates copolymer: polyquaternium-69; or
   a 1:10 to 20:1 ratio by weight of acrylates copolymer: vinyl pyrrolidone/methacrylamide/vinyl imidazole copolymer, wherein
   the hair styling composition comprises a Young's modulus above 150 MPa, an elongation at break of from about 15% to about 300% as measured by ASTM D638/ASTM D412, and a moisture uptake of less than 10%.

2. The hair styling composition of claim 1, wherein the composition consists essentially of
   a 1.5:1 ratio by weight of acrylates copolymer:corn starch modified;
   a 1.9:1 ratio by weight of acrylates copolymer:acrylates/octylacrylamide copolymer;
   a 4:1 ratio by weight of acrylates copolymer:polyvinylcaprolactam;
   a 1.5:1 ratio by weight of acrylates copolymer:octylacrylamide/acrylates/butylaminoethyl methacrylate copolymer;
   a 2.3:1 ratio by weight of acrylates copolymer:polyquaternium-69; or
   a 2.0:1 ratio by weight of acrylates copolymer:vinyl pyrrolidone/methacrylamide/vinyl imidazole copolymer.

3. The hair styling composition of claim 1, wherein the composition is an aqueous solution or aqueous dispersion.

4. The hair styling composition of claim 1, wherein the composition consists essentially of a 1.5:1 ratio by weight of acrylates copolymer:corn starch modified.

5. The hair styling composition of claim 1, wherein the composition consists essentially of a 1:10 to 20:1 ratio by weight of acrylates copolymer:acrylates/octylacrylamide copolymer.

6. The hair styling composition of claim 5, wherein the composition consists essentially of a 1.9:1 ratio by weight of acrylates copolymer:acrylates/octylacrylamide copolymer.

7. The hair styling composition of claim 1, wherein the composition consists essentially of a 1:2 to 50:1 ratio by weight of acrylates copolymer:polyvinylcaprolactam.

8. The hair styling composition of claim 7, wherein the composition consists essentially of a 4:1 ratio by weight of acrylates copolymer:polyvinylcaprolactam.

9. The hair styling composition of claim 1, wherein the composition consists essentially of a 1:1 to 100:1 ratio by weight of acrylates copolymer:octylacrylamide/acrylates/butylaminoethyl methacrylate copolymer.

10. The hair styling composition of claim 9, wherein the composition consists essentially of a 1.5:1 ratio by weight of acrylates copolymer:octylacrylamide/acrylates/butylaminoethyl methacrylate copolymer.

11. The hair styling composition of claim 1, wherein the composition consists essentially of a 1:10 to 20:1 ratio by weight of acrylates copolymer:polyquaternium-69.

12. The hair styling composition of claim 11, wherein the composition consists essentially of a 2.3:1 ratio by weight of acrylates copolymer:polyquaternium-69.

13. The hair styling composition of claim 1, wherein the composition consists essentially of a 1:10 to 20:1 ratio by weight of acrylates copolymer:vinyl pyrrolidone/methacrylamide/vinyl imidazole copolymer.

14. The hair styling composition of claim 13, wherein the composition comprises a 2.0:1 ratio by weight of acrylates copolymer:vinyl pyrrolidone/methacrylamide/vinyl imidazole copolymer.

* * * * *